US006995167B2

(12) United States Patent
Loch, III et al.

(10) Patent No.: US 6,995,167 B2
(45) Date of Patent: Feb. 7, 2006

(54) ARYLKYLAMINE SPIROFUROPYRIDINES USEFUL IN THERAPY

(75) Inventors: James T Loch, III, Hopkinton, MA (US); George B Mullen, Milford, MA (US); Eifion D Phillips, Worcester, MA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/529,654

(22) PCT Filed: Dec. 23, 1999

(86) PCT No.: PCT/SE99/02478

§ 371 (c)(1), (2), (4) Date: Apr. 18, 2000

(87) PCT Pub. No.: WO00/42044

PCT Pub. Date: Jul. 20, 2000

(65) Prior Publication Data

US 2003/0149065 A1 Aug. 7, 2003

(30) Foreign Application Priority Data

Jan. 15, 1999 (SE) .................................... 9900100

(51) Int. Cl.
*A61K 31/439* (2006.01)
*C07D 221/22* (2006.01)

(52) U.S. Cl. ........................................ 514/278; 546/18

(58) Field of Classification Search ................ 514/278; 546/18

See application file for complete search history.

(56) References Cited

U.S. PATENT DOCUMENTS 6,110,914 A * 8/2000 Phillips et al.
6,706,878 B2 * 3/2004 Phillips et al. ................ 544/70

FOREIGN PATENT DOCUMENTS

EP 0 311 131 4/1989
WO WO 9606098 A1 2/1996
WO WO 9705139 A1 2/1997
WO WO 97/41125 11/1997

OTHER PUBLICATIONS

CAS ONLINE display of structures 1-87 from WO 9903859, Phillips et al. Dec. 8, 1999.*
J. Med Chem vol. 39, 1996, Gunnar Nordvall et al, "3-(2-Benzofuranyl)quinclidin-2-ene Derivatives: Novel Muscarinic Antagonists", p. 3269-3277, compound 9.

* cited by examiner

*Primary Examiner*—Laura L. Stockton
(74) *Attorney, Agent, or Firm*—Kenneth F. Mitchell

(57) ABSTRACT

A compound of formula I,

I wherein $NRR_1$ is attached at the 5- or 6-position of the furopyridine ring; R is hydrogen, $C_1$–$C_4$ alkyl, or $COR_2$; $R_1$ is $(CH_2)_nAr$, $CH_2CH{=}CHAr$, or $CH_2C{\equiv}CAr$; n is 0 to 3; A is N or NO; Ar is a 5- or 6-membered aromatic or heteroaromatic ring which contains zero to four nitrogen atoms, zero to one oxygen atoms, and zero to one sulfur atoms; or an 8-, 9- or 10-membered fused aromatic or heteroaromatic ring system containing zero to four nitrogen atoms, zero to one oxygen atoms, and zero to one sulfur, any of which may optionally be substituted with one to two substitutents independently selected from: halogen, trifluoromethyl, or $C_1$–$C_4$ alkyl; $R_2$ is hydrogen, $C_1$–$C_4$ alkyl, $C_1$–$C_4$ alkoxy or phenyl ring optionally substituted with one to three of the following substituents: halogen, $C_1$–$C_4$ alkyl, $C_2$–$C_4$ alkenyl, $C_2$–$C_4$ alkynyl, OH; $OC_1$–$C_4$ alkyl, $CO_2R_5$, —CN, —$NO_2$, —$NR_3R_4$, or —$CF_3$; $R_3$, $R_4$ and $R_5$ may be hydrogen, $C_1$–$C_4$ alkyl, or phenyl ring optionally substituted with one to three of the following substituents: halogen, $C_1$–$C_4$ alkyl, $C_2$–$C_4$ alkenyl, $C_2$–$C_4$ alkynyl, OH; $OC_1$–$C_4$ alkyl, —CN, —$NO_2$, or —$CF_3$; and enantiomers thereof, and pharmaceutically acceptable salts thereof, processes for preparing them, composition containing them, and their use in therapy, especially in the treatment or prophylaxis of psychotic disorders and intellectual impairment disorders.

10 Claims, No Drawings

ARYLKYLAMINE SPIROFUROPYRIDINES USEFUL IN THERAPY

This is a National Phase of International Application No. PCT/SE99/02478, filed Dec. 23, 1999 which claims the benefit under 35 U.S.C. § 119(a–d) of Application No. 9900100-0, filed in Sweden on Jan. 15, 1999.

TECHNICAL FIELD

This invention relates to novel substituted amines of spirofuropyridines or pharmaceutically acceptable salts thereof, processes for preparing them, pharmaceutical compositions containing them and their use in therapy. A further object is to provide active compounds, which are potent ligands for nicotinic acetylcholine receptors (nAChR's).

BACKGROUND OF THE INVENTION

The use of compounds which bind nicotinic acetylcholine receptors in the treatment of a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41–50, Academic Press Inc., San Diego, Calif.; Williams et al. (1994) "Neuronal Nicotinic Acetylcholine Receptors," Drug News & Perspectives, vol. 7, pp. 205–223; and Lin and Meyer, "Recent Developments in Neuronal Nicotinic Acetylcholine Receptor Modulators", Exp. Opin. Ther. Patents. (1998), 8(8): 991–1015.

U.S. Pat. No. 5,468,875 discloses N-alkylcarbamic acid 1-azabicyclo[2.2.1]hept-3-yl esters which are centrally active muscarinic agents useful in the treatment of Alzheimer's disease and other disorders.

N-(2-alkoxyphenyl) carbamic acid 1-azabicyclo[2.2.2]octan-3-yl esters are disclosed in Pharmazie, vol. 48, 465–466 (1993) along with their local anesthetic activity. N-phenylcarbamic acid 1-azabicyclo[2.2.2]octan-3-yl esters substituted at the ortho position on the phenyl ring are described as local anaesthetics in *Acta Pharm. Suecica*, 7, 239–246 (1970).

Furopyridines useful in controlling synaptic transmission are disclosed in WO 97/05139.

DISCLOSURE OF THE INVENTION

According to the invention it has been found that compounds of formula I,

I

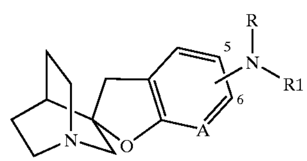

wherein $NRR_1$ is attached at the 5- or 6-position of the furopyridine ring;

R is hydrogen, $C_1$–$C_4$ alkyl, $COR_2$;

$R_1$ is $(CH_2)_nAr$, $CH_2CH{=}CHAr$, or $CH_2C{\equiv}CAr$;

n is 0 to 3;

A is N or NO;

Ar is a 5- or 6-membered aromatic or heteroaromatic ring which contains zero to four nitrogen atoms, zero to one oxygen atoms, and zero to one sulfur atoms;

or an 8-, 9- or 10-membered fused aromatic or heteroaromatic ring system containing zero to four nitrogen atoms, zero to one oxygen atoms, and zero to one sulfur atoms; any of which may optionally be substituted with one to two substituents independently selected from: halogen, trifluoromethyl, or $C_1$–$C_4$ alkyl;

$R_2$ is hydrogen, $C_1$–$C_4$ alkyl; $C_1$–$C_4$ alkoxy; or phenyl ring optionally substituted with one to three of the following substituents: halogen, $C_1$–$C_4$ alkyl, $C_2$–$C_4$ alkenyl, $C_2$–$C_4$ alkynyl, OH; $OC_1$–$C_4$ alkyl, $CO_2R_5$, —CN, —$NO_2$, —$NR_3R_4$, or —$CF_3$;

$R_3$, $R_4$ and $R_5$ are independently hydrogen; $C_1$–$C_4$ alkyl; or phenyl ring optionally substituted with one to three of the following substituents: halogen, $C_1$–$C_4$ alkyl, $C_2$–$C_4$ alkenyl, $C_2$–$C_4$ alkynyl, OH, $OC_1$–$C_4$ alkyl, $CO_2R_2$, —CN; —$NO_2$, or —$CF_3$;

or an enantiomer thereof, and pharmaceutically acceptable salts thereof, are potent ligands for nicotinic acetylcholine receptors.

Unless otherwise indicated, the $C_1$–$C_4$ alkyl groups referred to herein, e.g., methyl, ethyl, n-propyl, n-butyl, i-propyl, i-butyl, t-butyl, s-butyl, may be straight-chained or branched, and the $C_3$–$C_4$ alkyl groups may also be cyclic, e.g., cyclopropyl, cyclobutyl.

Unless otherwise indicated, the $C_1$–$C_4$ alkoxy groups referred to herein, e.g., methoxy, ethoxy, n-propoxy, i-propoxy, n-butoxy, i-butoxy, t-butoxy, s-butoxy, may be straight-chained or branched.

Unless otherwise indicated, the $C_2$–$C_4$ alkenyl groups referred to herein may contain one or two double bonds, e.g., ethenyl, i-propenyl, n-butenyl, i-butenyl, allyl, 1,3-butadienyl.

Unless otherwise indicated, the $C_2$–$C_4$ alkynyl groups referred to herein contain one triple bond, e.g., ethynyl, propynyl, 1- or 2-butynyl.

Halogen referred to herein may be fluoride, chloride, bromide, or iodide.

Unless otherwise indicated, (subst)phenyl refers to a phenyl ring optionally substituted with one to three of the following substituents: hydrogen, halogen, $C_1$–$C_4$ alkyl, $C_2$–$C_4$ alkenyl, $C_2$–$C_4$ alkynyl, OH, $OC_1$–$C_4$ alkyl, $CO_2R_5$, —CN, —$NO_2$, —$NR_3R_4$, —$CF_3$.

Preferred compounds of the invention are compounds of formula I wherein A is N.

Preferred compounds of the invention are compounds of formula I wherein $R_1$ is $(CH_2)_nAr$.

Preferred compounds of the invention are compounds of formula I wherein $R_1$ is $CH_2CH{=}CHAr$.

Preferred compounds of the invention are compounds of formula I wherein $R_1$ is $CH_2C{\equiv}CAr$.

Preferred compounds of the invention are compounds of formula I wherein Ar is selected from the group: phenyl ring optionally substituted with one to three of the following substituents: halogen, $C_1$–$C_4$ alkyl, $C_2$–$C_4$ alkenyl, $C_2$–$C_4$ alkynyl, OH, $OC_1$–$C_4$ alkyl, $CO_2R_5$, —CN, —$NO_2$, —$NR_3R_4$, and —$CF_3$; 2-, 3-, or 4-pyridyl; 2-, or 3-furanyl; 2-, or 3-thienyl; 2-, or 4-imidazolyl; 1, 2-, or 3-pyrrolyl; 2-, or 4-oxazolyl; and 3-, or 4-isoxazolyl.

Preferred compounds of the invention are compounds of formula I wherein Ar is selected from the group: 1-, or 2-naphthyl; 2-, 3-, 4-, 5-, 6-, 7-, or 8-quinolyl; 1-, 3-, 4-, 5-, 6-, 7-, or 8-isoquinolyl; 2-, 4-, 5-, 6-, or 7-benzoxazolyl; and 3-, 4-, 5-, 6-, or 7-benzisoxazolyl.

Preferred compounds of the invention are compounds of formula I, wherein $R_3$, $R_4$ and $R_5$ are independently hydrogen, or $C_1$–$C_4$ alkyl.

Preferred compounds of the invention are compounds of formula I wherein n is 1.

Preferred compounds of the invention are compounds of formula I wherein R is hydrogen.

Preferred compounds of the invention are compounds of formula I wherein Ar is an heteroaromatic ring.

Preferred compounds of the invention are compounds of formula I wherein n is 1, R is hydrogen and Ar is an heteroaromatic ring.

Preferred compounds of the invention include the following:

R-(−)-5'-N-(Phenylmethyl)aminospiro[1-azabicyclo[2.2.2]octane-3,2'-(3'H)-furo[2,3-b]pyridine];
R-(−)-5'-(2-Pyridylmethyl)aminospiro[1-azabicyclo[2.2.2]octane-3,2'-(3'H)-furo[2,3-b]pyridine];
R-(−)-5'-(3-Pyridylmethyl)aminospiro[1-azabicyclo[2.2.2]octane-3,2'-(3'H)-furo[2,3-b]pyridine];
R-(−)-5'-(4-pPyridylmethyl)aminospiro[1-azabicyclo[2.2.2]octane-3,2'-(3'H)-furo[2,3-b]pyridine];
R-(−)-5'-(2-Furanylmethyl)aminospiro[1-azabicyclo[2.2.2]octane-3,2'-(3'H)-furo[2,3-b]pyridine];
R-(−)-5'-(3-Furanylmethyl)aminospiro[1-azabicyclo[2.2.2]octane-3,2'-(3'H)-furo[2,3-b]pyridine];
R-(−)-5'-(2-Thienylmethyl)aminospiro[1-azabicyclo[2.2.2]octane-3,2'-(3'H)-furo[2,3-b]pyridine];
R-(−)-5'-(2-Imidazolylmethyl)aminospiro[1-azabicyclo[2.2.2]octane-3,2'-(3'H)-furo[2,3-b]pyridine];
R-(−)-5'-N-(4-Methoxyphenylmethyl)aminospiro[1-azabicyclo[2.2.2]octane-3,2'-(3'H)-furo[2,3-b]pyridine];
R-(−)-5'-N-(4-Chlorophenylmethyl)aminospiro[1-azabicyclo[2.2.2]octane-3,2'-(3'H)-furo[2,3-b]pyridine];
R-(−)-5'-N-(4-Methylphenylmethyl)aminospiro[1-azabicyclo[2.2.2]octane-3,2'-(3'H)-furo[2,3-b]pyridine];
R-(−)-5'-N-(3,4-Dichlorophenylmethyl)aminospiro[1-azabicyclo[2.2.2]octane-3,2'-(3'H)-furo[2,3-b]pyridine];
R-(−)-5'-N-Acetyl-N-(phenylmethyl)aminospiro[1-azabicyclo[2.2.2]octane-3,2'-(3'H)-furo[2,3-b]pyridine];
R-(−)-5'-N-Methyl-N-(phenylmethyl)aminospiro[1-azabicyclo[2.2.2]octane-3,2'-(3'H)-furo[2,3-b]pyridine];
R-(−)-5'-N-(3-Pyridyl)aminospiro[1-azabicyclo[2.2.2]octane-3,2'(3'H)-furo[2,3-b]pyridine];
R-(−)-6'-N-(Phenylmethyl)aminospiro[1-azabicyclo[2.2.2]octane-3,2'(3'H)-furo[2,3-b]pyridine];
R-(−)-5'-N-(3-Thienylmethyl)aminospiro[1-azabicyclo[2.2.2]octane-3,2'-(3'H)-furo[2,3-b]pyridine];
R-(−)-5'-N-(2-Phenylethyl)aminospiro[1-azabicyclo[2.2.2]octane-3,2'-(3'H)-furo[2,3-b]pyridine];
R-(−)-5'-N-(3-Phenylpropyl)aminospiro[1-azabicyclo[2.2.2]octane-3,2'-(3'H)-furo[2,3-b]pyridine];
R-(−)-5'-N-(Quinolin-3-ylmethyl)aminospiro[1-azabicyclo[2.2.2]octane-3,2'-(3'H)-furo[2,3-b]pyridine];
R-(−)-5'-N-(Quinolin-4-ylmethyl)aminospiro[1-azabicyclo[2.2.2]octane-3,2'-(3'H)-furo[2,3-b]pyridine];
R-(−)-5'-N-(1,4-Benzodioxan-6-ylmethyl)aminospiro[1-azabicyclo[2.2.2]octane-3,2'-(3'H)-furo[2,3-b]pyridine];
R-(−)-5'-N-(Imidazol-4-ylmethyl)aminospiro[1-azabicyclo[2.2.2]octane-3,2'-(3'H)-furo[2,3-b]pyridine];
R-(−)-5'-N-(trans-3-Phenylprop-2-enyl)aminospiro[1-azabicyclo[2.2.2]octane-3,2'-(3'H)-furo[2,3-b]pyridine];
R-(−)-5'-N-(Thiazol-2-ylmethyl)aminospiro[1-azabicyclo[2.2.2]octane-3,2'-(3'H)-furo[2,3-b]pyridine];
R-(−)-5'-N-(3-Methylphenylmethyl)aminospiro[1-azabicyclo[2.2.2]octane-3,2'-(3'H)-furo[2,3-b]pyridine];
R-(−)-5'-N-(2-Chlorophenylmethyl)aminospiro[1-azabicyclo[2.2.2]octane-3,2'-(3'H)-furo[2,3-b]pyridine];
R-(−)-5'-N-(3-Chlorophenylmethyl)aminospiro[1-azabicyclo[2.2.2]octane-3,2'-(3'H)-furo[2,3-b]pyridine];
R-(−)-5'-N-(3-Phenylpropynyl)aminospiro[1-azabicyclo[2.2.2]octane-3,2'-(3'H)-furo[2,3-b]pyridine];
R-(−)-5'-N-(3-Hydroxyphenylmethyl)aminospiro[1-azabicyclo[2.2.2]octane-3,2'-(3'H)-furo[2,3-b]pyridine];
R-(−)-5'-N-(4-Hydroxyphenylmethyl)aminospiro[1-azabicyclo[2.2.2]octane-3,2'-(3'H)-furo[2,3-b]pyridine];
R-(−)-5'-N-[trans-3-(4-Pyridinyl)prop-2-enyl]aminospiro[1-azabicyclo[2.2.2]octane-3,2'-(3'H)-furo[2,3-b]pyridine];
R-(−)-5'-N-Acetyl-N-(3-Thienylmethyl)aminospiro[1-azabicyclo[2.2.2]octane-3,2'-(3'H)-furo[2,3-b]pyridine];
R-(−)-5'-N-Methyl-N-(4-pyridylmethyl)aminospiro[1-azabicyclo[2.2.2]octane-3,2'-(3'H)-furo[2,3-b]pyridine];
R-(−)-5'-N-Methyl-N-(3-pyridylmethyl)aminospiro[1-azabicyclo[2.2.2]octane-3,2'-(3'H)-furo[2,3-b]pyridine];
R-(−)-5'-N-(2-Hydroxyethyl)-N-(3-thienylmethyl)aminospiro[1-azabicyclo[2.2.2]octane-3,2'-(3'H)-furo[2,3-b]pyridine];

and enantiomers thereof, and pharmaceutically acceptable salts thereof.

Particularly preferred compounds of the invention are compounds of formula I wherein n is 1; R is hydrogen and Ar is an heteroaromatic ring, including the following compounds:

R-(−)-5'-(3-Pyridylmethyl)aminospiro[1-azabicyclo[2.2.2]octane-3,2'-(3'H)-furo[2,3-b]pyridine];
R-(−)-5'-(4-Pyridylmethyl)aminospiro[1-azabicyclo[2.2.2]octane-3,2'-(3'H)-furo[2,3-b]pyridine];

and enantiomers thereof, and pharmaceutically acceptable salts thereof.

The compounds of the invention have the advantage that they may be less toxic, be more efficacious, be longer acting, have a broader range of activity, be more potent, produce fewer side effects, are more easily absorbed or have other useful pharmacological properties.

Methods of Preparation

In the reaction schemes and text that follow, R and $R_1$, unless otherwise indicated, are as defined above for formula I. Formula VIII represents a compound of formula I wherein $NRR_1$ is attached at the 5-position of the furopyridine ring. Formula IX represents a compound of formula I wherein $NRR_1$ is attached at the 6-position of the furopyridine ring. A represents N; E represents halogen, $NO_2$, or NHR. The compounds of formula I may be prepared according to the methods outlined in Scheme 1.

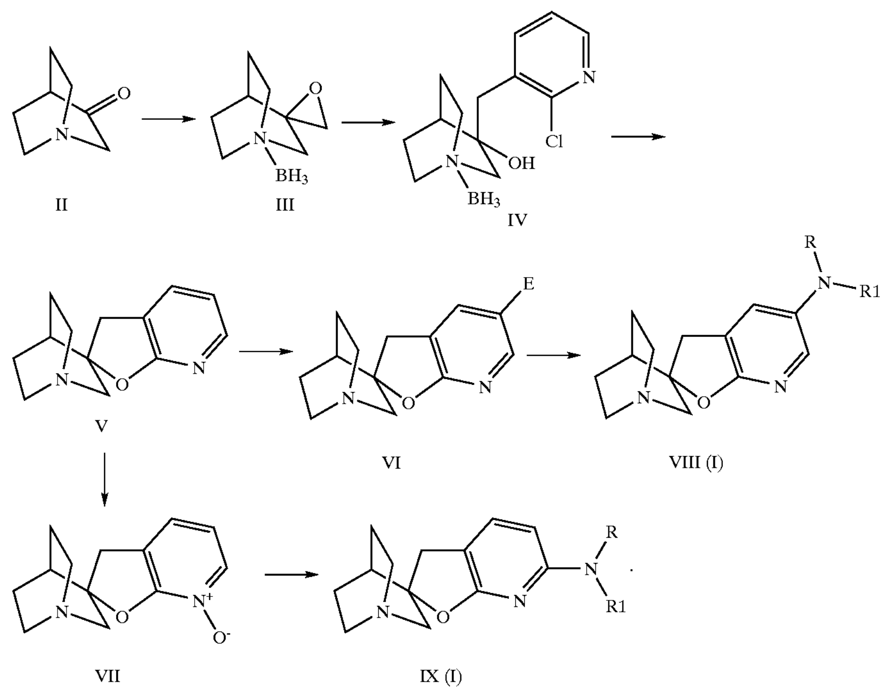

Compounds of formula I wherein A represents NO may be prepared from compounds of formula I wherein A represents N by oxidation with a peroxidic reagent in a suitable solvent, followed by reduction of the tertiary amine oxides in a suitable solvent. Oxidizing agents include hydrogen peroxide, m-chloroperbenzoic acid, peracetic acid, or magnesium monoperoxyphthalate. The preferred oxidant is m-chloroperbenzoic acid. Suitable inert solvents include chloroform, methylene chloride, and 1,2-dichloroethane. The preferred solvent is dichloromethane. The reaction is usually conducted at a temperature from −20° C. to 66° C., preferably from 0° C. to 20° C. Reducing agents include sulfur dioxide and triphenylphosphine. The preferred reagent is sulfur dioxide. Suitable inert solvents include water and alcohols. The preferred solvent is ethanol. The reaction is usually conducted at a temperature from −20° C. to 50° C., preferably from 0° C. to 25° C.

Compounds of formula I wherein R represents $COR_2$ may be prepared from compounds of formula I wherein R represents hydrogen using a suitable acylation procedure. Typical acylation procedures include treatment with a carboxylic acid and a coupling agent, for example dicyclohexylcarbodiimide, in a suitable solvent, for example tetrahydrofuran, or treatment with a carboxylic acid chloride or anhydride in the presence of a base. The preferred method is treatment with a carboxylic anhydride. Suitable bases include triethylamine, 4-(N,N-dimethylamino)pyridine, or pyridine. The preferred base is pyridine. The reaction is usually conducted at a temperature of 0° C. to 120° C., preferably from 80° C. to 100° C.

Compounds IX may be prepared from compound VII by reaction with a halogenating reagent such as phosphorus oxychloride, phosphorus oxybromide, phosphorus pentachloride or phosphorus pentabromide, followed by reaction with an amine in an inert solvent. The preferred halogenating agent is phosphorus oxychloride. The halogenating reaction is usually conducted at a temperature from 0° C. to 150° C., preferably from 80° C. to 120° C. The amine component may be any amine $NHRR_1$ defined as above. Suitable inert solvents include alcoholic solvents such as methanol and ethanol, as well as aromatic solvents such as benzene, toluene or xylene. The preferred inert solvent is ethanol. The reaction is usually conducted at a temperature from 20° C. to 200° C., preferably from 100° C. to 170° C. The reaction with the amine may be facilitated by the presence of a suitable organometallic catalyst and a base. Suitable organometallic catalysts include palladium phosphine complexes, which may be formed in situ from a source of palladium and a suitable phosphine. The preferred source of palladium is tris(dibenzylidineacetone)dipalladium (0). The preferred phosphine is 2-2'-bis(diphenylphosphino)1,1'-binaphthyl. Suitable bases include lithium bis(trimethylsilyl)amide, or sodium t-butoxide, preferably sodium t-butoxide. Suitable inert solvents for the reaction in the presence of an organometallic catalyst include tetrahydrofuran, 1,2-dimethoxyethane, or 1,4-dioxane, preferably 1,2-dimethoxyethane, and the reaction is usually conducted at a temperature of 60° C. to 120° C., preferably from 80° C. to 110° C.

Compounds of formula VIII may be prepared from compounds of formula VI wherein E represents NHR by a suitable alkylation procedure. Typical alkylation procedures include treatment with an appropriate alkyl halide or sulfonate ester and base, for example sodium hydride, in a suitable solvent, for example DMF, or reductive alkylation using the appropriate aromatic aldehyde together with a suitable reducing agent in an inert solvent. The preferred method is reductive alkylation. Suitable aromatic aldehydes include $Ar(CH_2)_mCHO$, ArCH═CHCHO, or ArC≡CCHO, where m may be 0–2 and Ar is defined as above. Suitable reductive alkylating agents include sodium borohydride and sodium cyanoborohydride. The preferred reducing agent is sodium borohydride. Suitable inert solvents include water, methanol or ethanol. The preferred solvent is methanol. The reaction is usually conducted at a temperature of 0° C. to 100° C., preferably from 20° C. to 65° C.

Compounds of formula VIII may be prepared from compounds of formula VI wherein E represents halogen by reaction with an amine of formula $RR_1NH$ in the presence of a suitable organometallic catalyst, base, and solvent. Suitable organometallic catalysts include palladium phosphine complexes, which may be formed in situ from a source of palladium and a suitable phosphine. The preferred source of palladium is tris(dibenzylidineacetone)dipalladium (0). The preferred phosphine is 2-2'-bis(diphenylphosphino)1,1'-binaphthyl. Suitable bases include lithium bis(trimethylsilyl)amide, or sodium t-butoxide, preferably sodium t-butoxide. Suitable inert solvents include tetrahydrofuran, 1,2-dimethoxyethane, or 1,4-dioxane. The preferred solvent is 1,2-dimethoxyethane. The reaction is usually conducted at a temperature of 60° C. to 120° C., preferably from 80° C. to 110° C.

Compound VII may be prepared from compound V by oxidation with a peroxidic reagent in a suitable solvent, followed by reduction of the tertiary amine oxides in a suitable solvent. Oxidizing agents include hydrogen peroxide, m-chloroperbenzoic acid peracetic acid, or magnesium monoperoxyphthalate. The preferred oxidant is m-chloroperbenzoic acid. Suitable inert solvents include chloroform, methylene chloride, and 1,2-dichloroethane. The preferred solvent is dichloromethane. The reaction is usually conducted at a temperature from −20° C. to 66° C., preferably from 0° C. to 20° C. Reducing agents include sulfur dioxide and triphenylphosphine. The preferred reagent is sulfur dioxide. Suitable inert solvents include water and alcohols. The preferred solvent is ethanol. The reaction is usually conducted at a temperature from −20° C. to 50° C., preferably from 0° C. to 25° C.

Compounds of formula VI wherein E represents NHR and R represents an alkyl group may be prepared from compounds of formula VI wherein E represents $NH_2$ by a suitable alkylation procedure. Typical alkylation procedures include treatment with an appropriate alkyl halide or sulfonate ester and base, for example sodium hydride, in a suitable solvent, for example DMF, or reductive alkylation using the appropriate aldehyde or ketone together with a suitable reducing agent in an inert solvent. The preferred method is reductive alkylation. Suitable reducing agents include sodium borohydride and sodium cyanoborohydride. The preferred reducing agent is sodium borohydride. Suitable inert solvents include water, methanol or ethanol. The preferred solvent is methanol. The reaction is usually conducted at a temperature of 0° C. to 100° C., preferably from 20° C. to 65° C.

Compounds of formula VI wherein E represents $NH_2$ may be prepared from compounds of formula VI wherein E represents $NO_2$ by reduction in a suitable solvent. Suitable reducing agents include hydrogen in the presence of a catalyst, for example 5–10% palladium on carbon, platinum oxide, or rhodium on carbon. The preferred reducing agent is hydrogen in the presence of 10% palladium on carbon. Suitably inert solvents include water, methanol or ethanol. The preferred solvent is methanol. The reaction is usually conducted at a temperature of 0° C. to 65° C., preferably 15° C. to 30° C.

Compound VI wherein E represents $NO_2$ may be prepared from compound V by reaction with a nitrating agent in an appropriate solvent. The preferred nitrating agent is fuming nitric acid; the preferred solvent is sulfuric acid. The reaction is usually conducted at a temperature from −10° C. to 100° C., preferably from 50° C. to 80° C.

Compounds of formula VI wherein E represents halogen may be prepared from a compound V by reaction with a halogenating agent in a suitable solvent, for example bromine in acetic acid. The reaction is usually carried out at a temperature of 0° C. to 110° C., preferably from 60° C. to 110° C.

Compound V may be prepared from the cyclization of compound IV in the presence of a base in an inert solvent, followed by deprotection of the cyclized compound using acid in a suitable solvent. Suitable bases include sodium hydride, sodium amide, potassium hydride, potassium t-amylate, potassium t-butoxide, and potassium bis(trimethylsilyl)amide. The preferred base is sodium hydride. Suitable inert solvents include N,N-dimethylformamide, N-methylpyrrolidin-2-one, ethers such as diethyl ether, tetrahydrofuran, and 1,4-dioxane, and dimethylsulfoxide. The preferred inert solvent is N,N-dimethylformamide. The reaction is usually conducted at a temperature from −10° C. to 100° C., preferably from 20° C. to 66° C.

Suitable acids for the deprotection of the cyclized compound include mineral, organic and Lewis acids, for example, hydrochloric and hydrobromic acid, sulfuric acid, triflic acid, methanesulfonic acid, and boron trifluoride etherate. The preferred acid is hydrobromic acid. Suitable solvents include acetone, butanone, ethanone, and pinacolone. The preferred solvent is acetone. The reaction is usually conducted at a temperature from −10° C. to 100° C., preferably from 0° C. to 60° C. Alternatively the deprotection may be conducted by heating the borane complex in alcoholic solvents. A preferred method is by refluxing an ethanolic solution of the complex.

Compound IV may be prepared from compound III using a lithium base and a proton transfer agent in an inert solvent. Suitable lithium bases include lithium diisopropylamine n-butyllithium, sec-butyllithium, tert-butyllithium, and phenyllithium. The preferred lithium base is phenyllithium. Suitable proton transfer agents include hindered secondary amines such as diisopropylamine and 2,2,6,6-tetramethylpiperidine. The preferred proton transfer agent is diisopropylamine. Suitable inert solvents include diethyl ether, tetrahydrofuran and 1,4-dioxane. The preferred inert solvent is tetrahydrofuran. The reaction is usually conducted at a temperature from −100° C. to 0° C., preferably from −78° C. to −25° C.

Compound III may be prepared from the reaction of compound II with an anion of a reagent well known in the art for the preparation of oxiranes from ketones (see e.g. the reactions referenced in J. March, "Advanced Organic Chemistry" (1992) $4^{th}$ Edition, pages 974–975), followed by reaction with borane ($BH_3$ or $B_2H_6$) in an inert solvent, Borane in tetrahydrofuran is preferred. Suitable inert solvents include diethyl ether, tetrahydrofuran and 1,4-dioxane. The preferred inert solvent is tetrahydrofuran. The reaction is usually conducted at a temperature from −10° C. to 66° C., preferably from 0° C. to 20° C. Suitable epoxidizing agents include trimethylsulfoxonium iodide, trimethylsulfonium iodide and diazomethane. The preferred reagent is trimethylsulfoxonium iodide. Suitable inert solvents include dipolar aprotic solvents. The preferred solvent is dimethylsulfoxide. The reaction is usually conducted at a temperature from −10° C. to 100° C., preferably from 50° C. to 75° C.

Where necessary, hydroxy, amino, or other reactive groups may be protected using a protecting group as described in the standard text "Protecting groups in Organic Synthesis", $2^{nd}$ Edition (1991) by Greene and Wuts.

The above described reactions, unless otherwise noted, are usually conducted at a pressure of one to three atmospheres, preferably at ambient pressure (about one atmosphere). Unless otherwise stated, the above-described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

Intermediates

A further aspect of the invention relates to new intermediates. Special interest among these new intermediates are the compounds of formula VI and VII in Scheme I. These intermediates are useful in the synthesis of compounds of formula I, but their use is not limited to the synthesis of said compounds. The formulas for these compounds are presented below:

Compounds of formula VI

VI

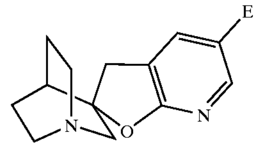

where E is $NO_2$, NHR or halogen;

and compounds of formula VII

VII

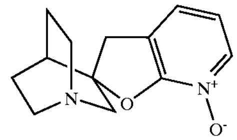

Intermediate compounds also exist in enantiomeric forms and may be used as purified enantiomers, racemates or mixtures.

Use of compounds VI and VII as intermediates in a synthesis of a ligand for nicotinic acetylcholine receptors is another aspect of the invention.

Pharmaceutical Compositions

A further aspect of the invention relates to a pharmaceutical composition for treating or preventing a condition or disorder as exemplified below arising from dysfunction of nicotinic acetylcholine receptor neurotransmission in a mammal, preferably a human, comprising an amount of a compound of formula I, an enantiomer thereof, and a pharmaceutically acceptable salt thereof, effective in treating or preventing such disorder or condition and an inert pharmaceutically acceptable carrier.

For the above-mentioned uses the dosage administered will, of course, vary with the compound employed, the mode of administration and the treatment desired. However, in general, satisfactory results will be obtained when the compounds of the invention are administered at a daily dosage of from 0.1 mg to 20 mg per kg of mammalian body weight, preferably given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carrier or diluent.

The compounds of formula I, or an enantiomer thereof, and pharmaceutically acceptable salts thereof, may be used on their own or in the form of appropriate medicinal preparations for enteral, parenteral, oral, rectal or nasal administration. According to a further aspect of the invention, there is provided a pharmaceutical composition preferably comprising less than 80% and more preferably less than 50% by weight of a compound of the invention in admixture with an inert pharmaceutically acceptable diluent or carrier.

Examples of suitable diluents and carriers are:

for tablets and dragees: lactose, starch, talc, stearic acid; for capsules: tartaric acid or lactose;

for injectable solutions: water, alcohols, glycerin, vegetable oils; for suppositories: natural or hardened oils or waxes.

There is also provided a process for the preparation of such a pharmaceutical composition, which comprises mixing the ingredients simultaneously or sequentially.

Utility

A further aspect of the invention is the use of a compound according to the invention, or an enantiomer thereof, and a pharmaceutically acceptable salt thereof, in the manufacture of a medicament for the treatment or prophylaxis of one of the below mentioned diseases or conditions; and a method of treatment or prophylaxis of one of the below mentioned diseases or conditions, which comprises administering a therapeutically effective amount of a compound according to the invention, or an enantiomer thereof, and a pharmaceutically acceptable salt thereof, to a patient.

Compounds according to the invention are agonists of nicotinic acetylcholine receptors. While not being limited by theory, it is believed that agonists of the α7 nAChR (nicotinic acetylcholine receptor) subtype should be useful in the treatment or prophylaxis of psychotic disorders and intellectual impairment disorders, and have advantages over compounds which are, or are also agonists of the α4 nAChR subtype. Therefore, compounds which are selective for the α7 nAChR subtype are preferred. The compounds of the invention are selective for the α7 nAChR subtype. The compounds of the invention are intended as pharmaceuticals, in particular in the treatment or prophylaxis of psychotic disorders and intellectual impairment disorders. Examples of psychotic disorders include schizophrenia, mania or manic depression, and anxiety. Examples of intellectual impairment disorders include Alzheimer's disease, learning deficit, cognition deficit, attention deficit, memory loss, Lewy Body Dementia, and Attention Deficit Hyperactivity Disorder. The compounds of the invention may also be useful as analgesics in the treatment of pain (including chronic pain) and in the treatment or prophylaxis of Parkinson's disease, Huntington's disease, Tourette's syndrome, and neurodegenerative disorders in which there is loss of cholinergic synapses. The compounds may further be indicated for the treatment or prophylaxis of jetlag, for use in inducing the cessation of smoking, and for the treatment or prophylaxis of nicotine addiction (including that resulting from exposure to products containing nicotine).

It is also believed that compounds according to the invention are useful in the treatment and prophylaxis of ulcerative colitis.

Pharmacology

The pharmacological activity of the compounds of the invention may be measured in the tests set out below:

Test A—Assay for Affinity at α7 nAChR Subtype $^{125}$I-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000×g, the supernatant was saved and the pellet re-extracted. The pooled supernatants were centrifuged for 20 minutes at 12,000×g, washed, and resuspended in HB. Membranes (30–80 μg) were incubated with 5 nM [$^{125}$I]α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine)) in water was critical for low filter blanks (0.07% of total counts per minute). Nonspecific binding was described by 100 μM (−)-nicotine, and specific binding was typically 75%.

Test B—Assay for Affinity to the α4 nAChR Subtype

[$^3$H]-(−)-nicotine binding. Using a procedure modified from Martino-Barrows and Kellar (Mol Pharm (1987) 31:169–174), rat brain (cortex and hippocampus) was homogenized as in the [$^{125}$I]α-BTX binding assay, centrifuged for 20 minutes at 12,000×g, washed twice, and then resuspended in HB containing 100 μM diisopropyl fluorophosphate. After 20 minutes at 4° C., membranes (approximately 0.5 mg) were incubated with 3 nM [3H]-(−)-nicotine, test drug, 1 μM atropine, and either 2 mM $CaCl_2$ or 0.5 mM EGTA for 1 hour at 4° C., and then filtered over Whatman glass fibre filters (thickness C) (pretreated for 1 hour with 0.5% PEI) using a Brandel cell harvester. Nonspecific binding was described by 100 μM carbachol, and specific binding was typically 84%.

Binding Data Analysis for Tests A and B $IC_{50}$ values and pseudo Hill coefficients ($n_H$) were calculated using the non-linear curve fitting program ALLFIT (DeLean A, Munson P J and Rodbard D (1977) Am. J. Physiol., 235:E97–E102). Saturation curves were fitted to a one site model, using the non-linear regression program ENZFITTER (Leatherbarrow, R. J. (1987)), yielding $K_D$ values of 1.67 and 1.70 nM for the $^{125}$I-α-BTX and [$^3$H]-(−)-nicotine ligands respectively. $K_i$ values were estimated using the general Cheng-Prusoff equation:

$$K_i-[IC_{50}]/((2+([ligand]/[K_D])^n)^{1/n}-1)$$

where a value of n=1 was used whenever $n_H<1.5$ and a value of n=2 was used when $n_H\geqq 1.5$. Samples were assayed in triplicate and were typically ±5%. $K_i$ values were determined using 6 or more drug concentrations. The compounds of the invention are compounds with binding affinities ($K_i$) of less than 1000 nM in either Test A or Test B, indicating that they are expected to have useful therapeutic activity.

EXAMPLES

Commercial reagents were used without further purification. Mass spectra were recorded using either a Hewlett Packard 5988A or a MicroMass Quattro-1 Mass Spectrometer and are reported as m/z for the parent molecular ion with its relative intensity. Room temperature refers to 20–25° C.

The following examples are preferred non-limiting examples embodying preferred aspects of the invention.

Preparation 1

Spiro[1-azabicyclo[2.2.2]octane-3,2'-oxirane] N-borane complex (compound III)

A mixture of trimethylsulfoxonium iodide (16.10 g, 73.2 mmol) and a dispersion of sodium hydride (60% in oil, 3.00 g, 75.0 mmol) in anhydrous dimethyl sulfoxide was stirred at room temperature under nitrogen for 30 minutes. Quinuclidin-3-one (II) (7.05 g, 56.3 mmol) was then added as a solid portionwise, and the resulting mixture was stirred at 65–70° C. under nitrogen for 1 hour. The reaction mixture was cooled, water was added (200 ml), and the resulting solution was extracted with chloroform (3×200 ml). The chloroform extracts were combined, and back-extracted with water (4×200 ml). The chloroform layer was then dried ($MgSO_4$), filtered, and evaporated under reduced pressure to afford spiro[1-azabicyclo[2.2.2]octane-3,2'-oxirane] (6.51 g, 46.8 mmol, 83%) as a clear, colorless liquid. To a stirred solution of spiro[1-azabicyclo[2.2.2]octane-3,2'-oxirane] (5.3 g, 38.1 mmol) in anhydrous tetrahydrofuran (100 ml) at 0° C. was added dropwise a solution of borane in tetrahydrofuran (1.0 M, 38.1 ml, 38.1 mmol), and resulting solution was stirred at 0° C. under nitrogen for 30 minutes. Brine (100 ml) was added cautiously to the reaction solution, and the resulting aqueous mixture was extracted with ethyl acetate (2×100 ml). The organic extracts were combined, dried ($MgSO_4$), filtered, and evaporated under reduced pressure to afford the title compound (III) (4.3 g, 28.1 mmol, 74%) as a white solid: electrospray MS 152 ($[M-H]^+$, 15).

Preparation 2

3-(2-Chloropyridin-3-ylmethyl)-3-hydroxy-1-azabicyclo[2.2.2]octane N-borane complex (compound IV)

A solution of phenyllithium (1.8 M in cyclohexane/ether [7:3], 167 ml, 0.3 mol, 3 eq.) was added via a cannula to anhydrous tetrahydrofuran (350 ml) at −60° C. under a nitrogen atmosphere. Then, diisopropylamine (0.7 ml, 5 mmol) was added dropwise, followed by a dropwise addition of 2-chloropyridine (28.4 ml, 0.3 mol, 3 eq.) over ten minutes. The resulting solution was stirred at −40° C. under nitrogen for 1.5 hours. The solution was then cooled to −60° C., and a solution of spiro[1-azabicyclo[2.2.2]octane-3,2'-oxirane] N-borane complex (15.3 g, 0.1 mol) in tetrahydrofuran (75 ml) was added dropwise. The resulting reaction mixture was then stirred at −40° C. under nitrogen. After 3 hours, a saturated solution of sodium bicarbonate (150 ml) was slowly added, followed by water (400 ml), and the resulting aqueous mixture was allowed to warm to room temperature. The layers were separated and the aqueous phase was extracted with ethyl acetate (3×100 ml). The organic layers were combined, dried ($MgSO_4$), filtered, and evaporated under reduced pressure. Column chromatography using silica gel and elution with ethyl acetate/hexanes [3:2] afforded the title compound IV as a tan solid (17.5 g, 65.6 mmol, 66%): electrospray MS 269 ($[MH]^+$ with $^{37}Cl$, 10), 267 ($[MH]^+$ with $^{35}Cl$, 26).

Preparation 3

Spiro[1-azabicyclo[2.2.2]octane-3,2'(3'H)-furo[2,3-b]pyridine] (compound V)

3-(2-Chloropyridin-3-ylmethyl)-3-hydroxy-1-azabicyclo[2.2.2]octane N-borane complex (17.4 g, 65.3 mmol) was dissolved in anhydrous N,N-dimethylformamide (500 ml), the resulting solution was cooled to 0° C. under nitrogen, and a dispersion of sodium hydride (60% in oil, 6.55 g, 163 mmol, 2.5 eq.) was added portionwise. The resulting solution was stirred at room temperature under nitrogen for 16 hours. A saturated solution of ammonium chloride (50 ml) was then added at 0° C., followed by ice water (500 ml), and the resulting aqueous mixture was extracted with chloroform (4×125 mL). The organic extracts were combined, dried ($MgSO_4$), and evaporated under reduced pressure to afford an orange solid. Purification through a short column of silica gel eluting with chloroform/acetone [95:5 to 85:15], followed by stirring in hexanes (100 ml) and filtration, provided a yellow solid (12.7 g, 55.2 mmol, 84%) of spiro[1-azabicyclo[2.2.0]octane-3,2'(3'H)-furo[2,3-b]pyridine] N-borane complex, electrospray MS 231 ($[MH]^+$, 65). Spiro[1-azabicyclo[2.2.2]octane-3,2'(3'H)-furo[2,3-b]pyridine] N-borane complex (12.2 g, 53 mmol) was dissolved in 150 ml of acetone, the solution was cooled to 0° C., and an aqueous solution of HBr (24%; 50 mL) was added. The resulting solution was stirred at room temperature under nitrogen for 24 hours. The reaction was concentrated under reduced pressure, and the aqueous residue was treated with saturated aqueous sodium carbonate solution (50 ml). The solution was basified to pH>10 using solid sodium carbonate, and the resulting solution was extracted with chloroform (3×100 ml). The organic extracts were combined, dried ($MgSO_4$), filtered, and evaporated under reduced pressure to afford the title compound VI (11.2 g, 51.8 mmol, 98%, 54% overall) as an off-white solid: electrospray MS 217 ($[MH]^+$, 72).

The title compound was separated into its (R)- and (S)-enantiomers by either of the following methods:

Method A—250 mg of the title compound was separated by chiral HPLC, using a 2 cm×25 cm CHIRALCEL-OD column on a Waters Delta Prep 3000 Preparative Chromatography System, eluting with 2,2,4-trimethylpentane/ethanol (92:8 to 9:1) at a flow rate of 20 ml/min. This provided 111 mg of the (S)-enantiomer ($[\alpha]^{23}$=+59.7 (c=1, methanol)) and 90 mg of the (R)-enantiomer ($[\alpha]^{23}$=−63.9 (c=1, methanol)).

Method B—1 g (4.62 mmol) of the title compound was treated with L-(+)-tartaric acid (694 mg; 4.62 mmol) in 15% aqueous ethanol (10 ml) and recrystallized three times to obtain the (S)-enantiomer L-(+)-tartrate (650 mg; 1.77 mmol; $[\alpha]^{23}$=+57.7 (c=2, $H_2O$)). The filtrates were concentrated under reduced pressure and the aqueous residue was basified to pH>10 using solid sodium carbonate. The resulting mixture was extracted with chloroform (3×25 ml) and the combined extracts were dried ($MgSO_4$), and evaporated under reduced pressure. The residue (650 mg; 3 mmol) was treated with D-(−)-tartaric acid (452 mg; 3 mmol) and recrystallized as above to provide the (R)-enantiomer D-(−)-tartrate (775 mg; 2.11 mmol; $[\alpha]^{23}$=−58.2° (c=2, $H_2O$)).

Preparation 4

(R)-(−)-5'-Nitrospiro[1-azabicyclo[2.2.2]octane-3,2'(3'H)-furo[2,3-b]pyridine] (compound VI, E=$NO_2$)

(R)-(−)-Spiro[1-azabicyclo[2.2.2]octane-3,2'(3'H)-furo[2,3-b]pyridine] (3.03 g, 14 mmol) was dissolved in concentrated sulfuric acid (7 ml) at 0–5° C., fuming nitric acid (3.3 ml, 70.2 mmol) was added over 10 minutes, the mixture was stirred for 1 hour, and heated at 65–70° C. for 24 hours, cooled, poured onto ice (200 g), added 300 ml of water, basified to pH 10 with solid potassium carbonate, stirred for 1 hour, filtered off and dried, provided the solid title compound (3.6 g, 13.8 mmol, 98%): electrospray MS 262 ($[MH]^+$, 100).

Preparation 5

(R)-(−)-5'-Aminospiro[1-azabicyclo-[2.2.2]octane-3,2'(3'H)-furo[2,3-b]pyridine] (compound VI, E=$NH_2$)

A mixture of the enantiomer (R)-(−)-5'-nitrospiro[1-azabicyclo[2.2.2]octane-3,2'(3'H)-furo[2,3-b]pyridine] (3.8 g, 13.3 mmol) and 10% palladium on carbon (48% water wet, 270 g) in methanol (90 ml) was hydrogenated for 1 hour at 50 psi of hydrogen. The catalyst was filtered off through a pad of celite and the solvent was evaporated under reduced pressure; the residue was purified by flash chromatography (eluting with ammoniated chloroform/methanol, 95:5 to 85:15), provided the title compound (2.5 g, 10.8 mmol, 81%): electrospray MS (m/z, relative intensity) 232 ($[MH]^+$, 100).

Preparation 6

(R)-(−)-Spiro[1-azabicyclo[2.2.2]octane-3,2'(3'H)-furo[2,3-b]pyridine-N-oxide] (compound VII)

A solution of 2.03 g (9.38 mmol) of (R)-(−)-spiro[1-azabicyclo[2.2.2]octane-3,2'(3'H)-furo[2,3-b]pyridine] in 100 ml of methylene chloride was cooled in an ice bath, to which was added 6.90 g (22.8 mmol) of 57–86% m-chloroperbenzoic acid, in portions over 5 minutes. The reaction was allowed to warm gradually to ambient temperature and stirred for 24 hours total. The solvent was removed in vacuo and the solid residue was dissolved in 100 ml of absolute ethanol, cooled in an ice bath, and sulfur dioxide was bubbled in until the solution turned cloudy. The reaction was stirred for 4 hours, then the solvent was removed in vacuo. The solid residue was dissolved in 150 ml of a 9:1 mixture of chloroform and methanol, then extracted with 50 ml of 10% aqueous sodium hydroxide. The organic layer was dried over magnesium sulfate, concentrated in vacuo and flash chromatographed through neutral silica gel using a 9:1 mixture of chloroform and 2.0 M ammonia in methanol as the eluant, giving 1.30 g (60%) of the title compound following crystallization from ethyl acetate/hexane (1:1): $[\alpha]^{23}$=−56.82 (c=1.09, EtOH), electrospray MS 233 ($[MH]^+$, 100).

Preparation 7A

5'-Bromospiro[1-azabicyclo[2.2.2]octane-3,2'(3'H)-furo[2,3-b]pyridine] (compound VI, E=Br)

A solution of spiro[1-azabicyclo[2.2.2]octane-3,2'(3'H)-furo[2,3-b]pyridine] (100 mg, 0.462 mmol) and sodium acetate (410 mg, 5 mmol) in 50% aqueous acetic acid (4 ml) was heated to 60° C. Bromine (0.100 ml, 1.94 mmol) was added via a syringe over 10 minutes, and the solution was then heated under reflux for 1 hour. The mixture was allowed to cool to ambient temperature, basified to pH>10 with sodium carbonate, and extracted with chloroform (3×15 ml). The combined extracts were dried ($MgSO_4$), filtered, and evaporated under reduced pressure to give the title compound (110 mg, 0.37 mmol, 81%) as an off-white solid: electrospray MS 295 ($[MH]^+$, with $^{79}Br$, 100), 297 ($[MH]^+$, with $^{81}Br$, 98).

Preparation 7B

(R)-(−)-5'-Bromospiro[1-azabicyclo[2.2.2]octane-3,2'(3'H)-furo[2,3-b]pyridine] (compound VI, E=Br)

The enantiomer (R)-(−)-spiro[1-azabicyclo[2.2.2]octane-3,2'(3'H)-furo[2,3-b]pyridine] (1.95 g, 9 mmol) treated in the same way as described in preparation 7A provided the title compound (1.77 g, 6 mmol, 67%) ($[\alpha]^{23}$=−45.5° (c=1, MeOH)).

Example 1

R-(−)-5'-N-(Phenylmethyl)aminospiro[1-azabicyclo[2.2.2]octane-3,2'-(3'H)-furo[2,3-b]pyridine]

Sodium spheres were blotted dry of mineral spirits, weighed (100 mg, 4.3 mmol) and added gradually to 2 ml of anhydrous methanol, while stirring under a nitrogen atmosphere at 0° C. The reaction was stirred at 0° C. for 25 minutes, during which time the vigorous bubbling stopped and nearly all the solid dissolved. 5'-aminospiro[1-azabicyclo[2.2.2]octane-3,2'-(3'H)-furo[2,3-b]pyridine] (230 mg, 1.0 mmol) and benzaldehyde (0.23 ml, 1.0 mmol) were added, the ice bath was removed, and an additional 2 ml of anhydrous methanol was added. The solution was stirred at room temperature for two days, then heated to 50° C. for 2 hrs. Sodium borohydride (106 mg, 2.8 mmol) was added and the reaction was heated at reflux for 90 minutes. Upon cooling to ambient temperature, the methanol was removed in vacuo and the residue was partitioned between 8 ml of chloroform and 2 ml of water. The aqueous layer was extracted two more times with 8 ml of chloroform and the organic layers were combined and dried over magnesium sulfate. The chloroform was stripped in vacuo, and the crude product was purified on a silica flash column using a 0–10% ammoniated methanol/chloroform gradient, giving 0.25 g (77%) of the title compound as a white powder: electrospray MS 322 ($[MH]^+$, 100).

Example 2

R-(−)-5'-N-(2-Pyridylmethyl)aminospiro[1-azabicyclo[2.2.2]octane-3,2'-(3'H)-furo[2,3-b]pyridine]

The title compound was prepared by the procedure used in Example 1 from 115 mg (0.5 mmol) of 5'-aminospiro[1-azabicyclo[2.2.2]octane-3,2'-(3'H)-furo[2,3-b]pyridine] and 0.114 ml (1.2 mmol) of 2-pyridine carboxaldehyde to give 84 mg of the title compound as a beige powder (52%.): electrospray MS 323 ($[MH]^+$, 100).

Example 3

R-(−)-5'-N-(3-Pyridylmethyl)aminospiro[1-azabicyclo[2.2.2]octane-3,2'-(3'H)-furo[2,3-b]pyridine]

The title compound was prepared by the procedure used in Example 1 from 115 mg (0.5 mmol) of 5'-aminospiro[1-azabicyclo[2.2.2]octane-3,2'-(3'H)-furo[2,3-b]pyridine] and 3-pyridinecarboxaldehyde to give 81 mg, (50%) of the title compound as a beige powder: electrospray MS 323 ($[MH]^+$, 100).

Example 4

R-(−)-5'-N-(4-Pyridylmethyl)aminospiro[1-azabicyclo[2.2.2]octane-3,2'-(3'H)-furo[2,3-b]pyridine]

The title compound was prepared by the procedure used in Example 1 from 115 mg (0.5 mmol) of 5'-aminospiro[1-azabicyclo[2.2.2]octane-3,2'-(3'H)-furo[2,3-b]pyridine] and 4-pyridinecarboxaldehyde to give 84 mg, (52%) of the title compound as a light yellow powder: electrospray MS 323 ($[MH]^+$, 100).

Example 5

R-(−)-5'-N-(2-Furanylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of 5'-aminospiro[1-azabicyclo[2.2.2]octane-3,2'-(3'H)-furo[2,3-b]pyridine] and 2-furaldehyde (43 ml, 0.52 mmol), giving 30 mg of the title compound as a dark yellow semi-solid: electrospray MS 312 ($[MH]^+$, 100).

Example 6

R-(−)-5'-N-(3-Furanylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of 5'-aminospiro[1-azabicyclo[2.2.2]octane-3,2'-(3'H)-furo[2,3-b]pyridine] and 3-furaldehyde to give 25 mg of the title compound: electrospray MS 312 ($[MH]^+$, 100).

Example 7

R-(−)-5'-N-(2-Thienylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of 5'-aminospiro[1-azabicyclo[2.2.2]octane-3,2'-(3'H)-furo[2,3-b]pyridine] and 2-thiophenecarboxaldehyde, giving 9 mg of the title compound: electrospray MS 328 ($[MH]^+$, 100).

Example 8

R-(−)-5'-N-(4-Methoxyphenylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of 5'-aminospiro[1-azabicyclo[2.2.2]octane-3,2'-(3'H)-furo[2,3-b]pyridine] and 4-methoxybenzaldehyde, providing 18 mg of the title compound: electrospray MS 352 ($\{MH]^+$, 100).

Example 9

R-(−)-5'-N-(4-Chlorophenylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of 5'-aminospiro[1-azabicyclo[2.2.2]octane-3,2'-(3'H)-furo[2,3-b]pyridine] and 4-chlorobenzaldehyde to give 62 mg of the title compound: electrospray MS 356 $[MH]^+$, $^{37}Cl$ 358.

Example 10

R-(−)-5'-N-(4-Methylphenylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of 5'-aminospiro[1-azabicyclo[2.2.2]octane-3,2'-(3'H)-furo[2,3-b]pyridine] and 4-tolualdehyde, giving 6 mg of the title compound: electrospray MS 336 ($[MH]^+$, 100).

Example 11

R-(−)-5'-N-(3,4-Dichlorophenylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of 5'-aminospiro[1-azabicyclo[2.2.2]octane-3,2'-(3'H)-furo[2,3-b]pyridine] and 3,4-dichlorobenzaldehyde to give 19 mg of the title compound: electrospray MS 390 $[MH]^+$, $^{37}Cl_1$ 392, $^{37}Cl_2$ 394.

Example 12

R-(−)-5'-N-(2-Imidazolylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of 5'-aminospiro[1-azabicyclo[2.2.2]octane-3,2'-(3'H)-furo[2,3-b]pyridine] and 2-imidazolecarboxaldehyde, giving 57 mg of the title compound: electrospray MS 312 ($[MH]^+$, 100).

Example 13

R-(−)-5'-N-Acetyl-N-(phenylmethyl)aminospiro[1-azabicyclo[2.2.2]octane-3,2'-(3'H)-furo[2,3-b]pyridine]

Acetic anhydride (25 μl, 0.26 mmol) was added to a solution of R-(−)-5'-N-(phenylmethyl)aminospiro[1-azabicyclo[2.2.2]octane-3,2'-(3'H)-furo[2,3-b]pyridine] (50 mg, 0.22 mmol) in 1 ml of anhydrous pyridine under nitrogen. The reaction was heated at 95° C. with an oil bath, then cooled to ambient temperature and poured into saturated sodium carbonate. The product was extracted with four portions of chloroform. The organic layers were combined, dried over magnesium sulfate, and stripped in vacuo. The crude product was passed through a Supelco Visiprep using chloroform and then a 5–15% ammoniated methanol/chloroform gradient. The solvents were removed in vacuo, and the purified product was dissolved in methanol and acidified with 0.9 ml of 1.0 M hydrogen chloride in ether to provide 59 mg (61%) of the title compound as a white semi-solid: electrospray MS 364 ($[MH]^+$, 100).

Example 14

R-(−)-5'-N-Methyl-N-(phenylmethyl)aminospiro[1-azabicyclo[2.2.2]octane-3,2'-(3'H)-furo[2,3-b]pyridine]

Under a nitrogen atmosphere, sodium cyanoborohydride (39 mg, 0.62 mmol) was added to a solution of 50 mg, (0.22 mmol) of R-(−)-5'-N-(phenylmethyl)aminospiro[1-azabicyclo[2.2.2]octane-3,2'-(3'H)-furo[2,3-b]pyridine] and 165 μl (2.2 mmol) of 37% aqueous formaldehyde in 1 ml of deionized water adjusted to pH 3 using concentrated hydrochloric acid. The reaction was stirred at room temperature, adding acid to adjust the pH whenever it rose above 6. After one hour, the reaction was poured into saturated sodium carbonate and this was extracted with four portions of chloroform. The organic layers were combined, dried over magnesium sulfate, and stripped in vacuo. The residue was passed through a Supelco Visiprep using an ammoniated methanol/chloroform gradient. The solvents were removed in vacuo, and residue was taken up in methanol and acidified with 0.9 ml of 1.0 M hydrogen chloride in ether. Removal of the solvent in vacuo gave 64 mg (98%) of the HCl salt of the title compound as a light yellow semi-solid: electrospray MS 336 ($[MH]^+$, 100).

Example 15

(R)-(−)-5'-N-(3-Pyridylamino)spiro[1-azabicyclo[2.2.2]octane-3,2'(3'H)-furo[2,3-b]pyridine]

In a pressure tube sealed under nitrogen, (R)-(−)-5'-bromospiro[1-azabicyclo[2.2.2]octane-3,2'(3'H)-furo[2,3-b]pyridine] (105.1 mg, 0.36 mmol), 3-aminopyridine (69 mg, 0.73 mmol), tris(dibenzylidineacetone)dipalladium (0) (21 mg, 0.023 mmol), racemic-2-2'-bis(diphenylphosphino)1,1'-binaphthyl (34 mg, 0.055 mmol), sodium t-butoxide (0.105 g, 1.09 mmol), and 1,2-dimethoxyethane (5 ml) were heated and stirred at 100° C. After 3 days the solution was allowed to cool, and partitioned between water and chloroform. The chloroform layer was then dried by addition of magnesium sulfate and filtered through a solid phase extraction cartridge containing 5 g silica. The crude product was eluted from the cartridge with a 1:1 v/v mixture of methanolic ammonia and chloroform; the resulting solution was evaporated. The residue was purified by reverse phase HPLC on a C-18 column using a gradient of 0–50% acetonitrile and 0.1% aqueous trifluoroacetic acid as the eluant. The product-containing fractions were evaporated and the product was dissolved in a small volume of methanol (ca. 5 ml), and excess hydrogen chloride (1 M solution in ether, appr. 5 ml) was added. The solution was re-evaporated to give the title compound (54 mg, 0.13 mmol) as a hydrochloride salt: electrospray MS 309 ($[MH]^+$, 100); $[\alpha]_{589nm}=-42.0$ (c=0.1, MeOH).

Example 16

R-(−)-6'-N-(Phenylmethyl)aminospiro[1-azabicyclo[2.2.2]octane-3,2'-(3'H)-furo[2,3-b]pyridine]

(R)-(−)-spiro[1-azabicyclo[2.2.2]octane-3,2'(3'H)-furo[2,3-b]pyridine-N-oxide] (VII) [970 mg (4.20 mmol)] was dissolved in 10 ml of phosphorus oxychloride, while stirring in an ice bath. The suspension was then heated to reflux and stirred for 5 hours. Upon cooling to ambient temperature, the reaction was poured onto 100 g of ice, diluted with 100 ml of water, made basic with potassium carbonate, and extracted with chloroform (3×50 ml). The combined organic extract was dried over anhydrous magnesium sulfate, concentrated in vacuo, and flash chromatographed through neutral silica gel using a 95:5 mixture of chloroform and 2.0N ammonia in methanol to give 700 mg of (R)-(−)-6-chlorospiro[1-azabicyclo[2.2.2]octane-3,2'(3'H)-furo[2,3-b]pyridine] as an off white solid.

A solution of 85 mg (0.34 mmol) of the chloride in 3.0 ml of benzylamine was heated to reflux, under a nitrogen atmosphere, for 23 hours. Upon cooling to ambient temperature, the solution was flash chromatographed through neutral silica gel using a 9:1 mixture of chloroform and 2.0N ammonia in methanol, providing 22 mg (20%) of the title compound, electrospray MS 322 ($[MH]^+$, 100).

Example 17

R-(−)-5'-N-(3-Thienylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-aminospiro[1-azabicyclo[2.2.2]octane-3,2'-(3'H)-furo[2,3-b]pyridine] and 3-thiophenecarboxaldehyde, giving 61 mg (85%) of the title compound: electrospray MS 328 ($[MH]^+$, 100).

Example 18

R-(−)-5'-N-(2-Phenylethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-aminospiro[1-azabicyclo[2.2.2]octane-3,2'-(3'H)-furo[2,3-b]pyridine] and phenylacetaldehyde, giving 31 mg of the title compound: electrospray MS 336 ($[MH]^+$, 100).

Example 19

R-(−)-5'-N-(3-Phenylpropyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-aminospiro[1-azabicyclo[2.2.2]octane-3,2'-(3'H)-furo[2,3-b]pyridine] and 3-phenylpropionaldehyde, giving 42 mg of the title compound: electrospray MS 350 ($[MH]^+$, 100).

Example 20

R-(−)-5'-N-(Quinolin-3-ylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-aminospiro[1-azabicyclo[2.2.2]octane-3,2'-(3'H)-furo[2,3-b]pyridine] and 3-quinolinecarboxaldehyde, giving 47 mg of the title compound: electrospray MS 373 ($[MH]^+$, 100).

Example 21

R-(−)-5'-N-(Quinolin-4-ylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-aminospiro[1-azabicyclo[2.2.2]octane-3,2'-(3'H)-furo[2,3-b]pyridine] and 4-quinolinecarboxaldehyde, giving 3 mg of the title compound: electrospray MS 373 ($[MH]^+$, 100).

Example 22

R-(−)-5'-N-(1,4-Benzodioxan-6-ylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-amino spiro[1-azabicyclo[2.2.2]octane-3,2'-(3'H)-furo[2,3-b]pyridine] and 1,4-benzodioxan-6-ylcarboxaldehyde, giving 31 mg of the title compound: electrospray MS 380 ($[MH]^+$, 100).

Example 23

R-(−)-5'-N-(Imidazol-4-ylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-aminospiro[1-azabicyclo[2.2.2]octane-3,2'-(3'H)-furo[2,3-b]pyridine] and 4(5)-imidazolecarboxaldehyde, giving 1 mg of the title compound: electrospray MS 312 ($[MH]^+$, 100).

Example 24

R-(−)-5'-N-(trans-3-pyridinylprop-2-enyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-aminospiro[1-azabicyclo[2.2.2]octane-3,2'-(3'H)-furo[2,3-b]pyridine] and cinnamaldehyde, giving 43 mg of the title compound: electrospray MS 348 ($[MH]^+$, 100).

Example 25

R-(−)-5'-N-(Thiazol-2-ylmethyl)aminospiro[1-azabicyclo[2.2.2]octane-3,2'-(3'H)-furo[2,3-b]pyridine]

The title compound was prepared by the procedure used in Example 1 from 50 mg (0.22 mmol) of R-(−)-5'-aminospiro[1-azabicyclo[2.2.2]octane-3,2'-(3'H)-furo[2,3-b]pyridine] and 2-thiazolecarboxaldehyde, giving 13 mg of the title compound: electrospray MS 329 ($[MH]^+$, 100).

Example 26

R-(−)-5'-N-(3-Methylphenylmethyl)aminospiro[1-azabicyclo[2.2.2]octane-3,2'-(3'H)-furo[2,3-b]pyridine]

Titanium tetrachloride (0.5 ml of a 1.0 M solution in dichloromethane) was added to a solution of 50 mg (0.22 mmol) of R-(−)-5'-aminospiro[1-azabicyclo[2.2.2]octane-3,2'-(3'H)-furo[2,3-b]pyridine], 0.066 ml (0.47 mmol) of triethylamine and 0.026 ml (0.22 mmol) of m-tolualdehyde in 2 ml of chloroform, under a nitrogen atmosphere. After stirring for 16 h, a solution of 0.65 mmol of sodium cyanoborohydride in 0.55 ml of methanol was added; the resulting solution was stirred for 20 min, then poured into 20 ml of aqueous sodium carbonate and extracted with chloroform (4×10 ml). The combined organic extract was dried over magnesium sulfate, concentrated in vacuo and flash chromatographed through neutral silica gel using a 0–15% ammoniated methanol/chloroform gradient, giving 60 mg (81%) of the title compound: electrospray MS 336 ($[MH]^+$, 100).

Example 27

R-(−)-5'-N-(2-Chlorophenylmethyl)aminospiro[1-azabicyclo[2.2.2]octane-3,2'-(3'H)-furo[2,3-b]pyridine]

The title compound was prepared by the procedure used in Example 26 from 50 mg (0.22 mmol) of R-(−)-5'-aminospiro[1-azabicyclo[2.2.2]octane-3,2'-(3'H)-furo[2,3-b]pyridine] and 2-chlorobenzaldehyde, giving 63 mg of the title compound: electrospray MS 356 ($[MH]^+$, 100).

Example 28

R-(−)-5'-N-(3-Chlorophenylmethyl)aminospiro[1-azabicyclo[2.2.2]octane-3,2'-(3'H)-furo[2,3-b]pyridine]

The title compound was prepared by the procedure used in Example 26 from 50 mg (0.22 mmol) of R-(−)-5'-aminospiro[1-azabicyclo[2.2.2]octane-3,2'-(3'H)-furo[2,3-b]pyridine] and 2-chlorobenzaldehyde, giving 50 mg of the title compound: electrospray MS 356 ($[MH]^+$, 100).

Example 29

R-(−)-5'-N-(3-Phenylpropynyl)aminospiro[1-azabicyclo[2.2.2]octane-3,2'-(3'H)-furo[2,3-b]pyridine]

The title compound was prepared by the procedure used in Example 26 from 400 mg (1.76 mmol) of R-(−)-5'-aminospiro[1-azabicyclo[2.2.2]octane-3,2'-(3'H)-furo[2,3-b]pyridine] and 3-phenylpropargyl aldehyde, giving 212 mg of the title compound: electrospray MS 346 ($[MH]^+$, 100).

Example 30

R-(−)-5'-N-(3-Hydroxyphenylmethyl)aminospiro[1-azabicyclo[2.2.2]octane-3,2'-(3'H)-furo[2,3-b]pyridine]

The title compound was prepared by the procedure used in Example 26 from 250 mg (1.10 mmol) of R-(−)-5'-aminospiro[1-azabicyclo[2.2.2]octane-3,2'-(3'H)-furo[2,3-b]pyridine] and 3-hydroxybenzaldehyde, giving 117 mg of the title compound: electrospray MS 338 ($[MH]^+$, 100).

Example 31

R-(−)-5'-N-(4-Hydroxyphenylmethyl)aminospiro[1-azabicyclo[2.2.2]octane-3,2'-(3'H)-furo[2,3-b]pyridine]

The title compound was prepared by the procedure used in Example 26 from 250 mg (1.10 mmol) of R-(−)-5'-aminospiro[1-azabicyclo[2.2.2]octane-3,2'-(3'H)-furo[2,3-b]pyridine] and 4-hydroxybenzaldehyde, giving 31 mg of the title compound: electrospray MS 338 ($[MH]^+$, 100).

Example 32

R-(−)-5'-N-[trans-3-(4-Pyridinyl)prop-2-enyl]aminospiro[1-azabicyclo[2.2.2]octane-3,2'-(3'H)-furo[2,3-b]pyridine]

The title compound was prepared by the procedure used in Example 26 from 250 mg (1.10 mmol) of R-(−)-5'-aminospiro[1-azabicyclo[2.2.2]octane-3,2'-(3'H)-furo[2,3-b]pyridine] and trans-3-pyridylpropenal, giving 77 mg of the title compound: electrospray MS 349 ($[MH]^+$, 100).

Example 33

R-(−)-5'-N-Acetyl-N-(3-thienylmethyl)aminospiro[1-azabicyclo[2.2.2]octane-3,2'-(3'H)-furo[2,3-b]pyridine]

The title compound was prepared by the procedure used in Example 13 from 100 mg of R-(−)-5'-N-(3-thienylmethyl)aminospiro[1-azabicyclo[2.2.2]octane-3,2'-(3'H)-furo[2,3-b]pyridine] and acetic anhydride, giving 25 mg of the title compound: electrospray MS 370 ($[MH]^+$, 100).

Example 34

R-(−)-5'-N-Methyl-N-(4-pyridylmethyl)aminospiro[1-azabicyclo[2.2.2]octane-3,2'-(3'H)-furo[2,3-b]pyridine]

The title compound was prepared by the procedure used in Example 14 from 100 mg of R-(−)-5'-N-(4-pyridylmethyl)aminospiro[1-azabicyclo[2.2.2]octane-3,2'-(3'H)-furo[2,3-b]pyridine] and 37% aqueous formaldehyde, giving 26 mg of the title compound: electrospray MS 337 ($[MH]^+$, 100).

Example 35

R-(−)-5'-N-Methyl-N-(3-pyridylmethyl)aminospiro[1-azabicyclo[2.2.2]octane-3,2'-(3'H)-furo[2,3-b]pyridine]

The title compound was prepared by the procedure used in Example 14 from 200 mg of R-(−)-5'-N-(3-pyridylmethyl)aminospiro[1-azabicyclo[2.2.2]octane-3,2'-(3'H)-furo[2,3-b]pyridine] and 37% aqueous formaldehyde, giving 190 mg of the title compound: electrospray MS 337 ($[MH]^+$, 100).

Example 36

R-(−)-5'-N-(2-Hydroxyethyl)-N-(3-thienylmethyl)aminospiro[1-azabicyclo[2.2.2]octane-3,2'-(3'H)-furo[2,3-b]pyridine]

The title compound was prepared by the procedure used in Example 14 from 100 mg of R-(−)-5'-N-(3-thienylmethyl)aminospiro[1-azabicyclo[2.2.2]octane-3,2'-(3'H)-furo[2,3-b]pyridine] and glyoxal, giving 54 mg of the title compound: electrospray MS 372 ($[MH]^+$, 100).

What is claimed is:

1. A compound of formula I,

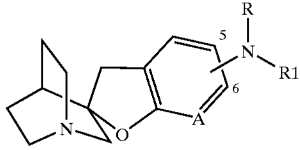

wherein $NRR^1$ is attached at the 5- or 6-position of the furopyridine ring;

R is hydrogen, $C_1$–$C_4$ alkyl, or $COR^2$;

$R^1$ is —$CH_2CH$═CHAr n is 0 to 3;

A is N;

Ar is a 5- or 6-membered aromatic or heteroaromatic ring which contains zero to four nitrogen atoms, zero to one oxygen atoms, and zero to one sulfur atoms which aromatic or heteroaromatic ring is optionally substituted with one to two substituents independently selected from: halogen, trifluoromethyl, or $C_1$–$C_4$alkyl;

$R^2$ is hydrogen, $C_1$–$C_4$alkyl; $C_1$–$C_4$alkoxy; or a phenyl ring optionally substituted with one to three of the following substituents: halogen, $C_1$–$C_4$alkyl, $C_2$–$C_4$alkenyl, $C_2$–$C_4$alkynyl, OH, —$OC_1$–$C_4$alkyl, —$CO_2R^5$, —CN, —$NO_2$, —$NR^3R^4$, or —$CF_3$;

$R^3$, $R^4$ and $R^5$ are independently hydrogen; $C_1$–$C_4$alkyl; or a phenyl ring optionally substituted with one to three of the following substituent: halogen, $C_1$–$C_4$alkyl, $C_2$–$C_4$alkenyl, $C_2$–$C_4$alkynyl, —OH, —$OC_1$–$C_4$alkyl, —CN, —$NO_2$, or —$CF_3$;

or an enantiomer thereof, or a pharmaceutically acceptable salt thereof.

2. A compound of formula I,

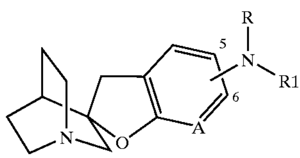

wherein $NRR^1$ is attached at the 5- or 6-position of the furopyridine ring;

R is hydrogen, $C_1$–$C_4$ alkyl, or $COR^2$;

$R^1$ is —$CH_2C$≡CAr n is 0 to 3;

A is N;

Ar is a 5- or 6-membered aromatic or heteroaromatic ring which contains zero to four nitrogen atoms, zero to one oxygen atoms, and zero to one sulfur atoms which aromatic or heteroaromatic ring is optionally substituted with one to two substituents independently selected from: halogen, trifluoromethyl, or $C_1$–$C_4$alkyl;

$R^2$ is hydrogen, $C_1$–$C_4$alkyl; $C_1$–$C_4$alkoxy; or a phenyl ring optionally substituted with one to three of the following substituents: halogen, $C_1$–$C_4$alkyl, $C_2$–$C_4$alkyenyl, $C_2$–$C_4$alkynyl, OH, —$OC_1$–$C_4$alkyl, —$CO_2R^5$, —CN, —$NO_2$, —$NR^3R^4$, or —$CF_3$;

$R^3$, $R^4$ and $R^5$ are independently hydrogen; $C_1$–$C_4$alkyl; or a phenyl ring optionally substituted with one to three of the following substituent: halogen, $C_1$–$C_4$alkyl, $C_2$–$C_4$alkenyl, $C_2$–$C_4$alkynyl, —OH, or —$OC_1$–$C_4$alkyl, —CN, —$NO_2$, or —$CF_3$;

or an enantiomer thereof, or a pharmaceutically acceptable salt thereof.

3. A compound selected from:

R-(−)-5'-(2-pyridylmethyl)aminospiro[1-azabicyclo [2.2.2]octane-3,2'-(3'H)-furo[2,3-b]pyridine];

R-(−)-5'-(3-pyridylmethyl)aminospiro[1-azabicyclo [2.2.2]octane-3,2'-(3'H)-furo[2,3-b]pyridine];

R-(−)-5'-(4-pyridylmethyl)aminospiro[1-azabicyclo [2.2.2]octane-3,2'-(3'H)-furo[2,3-b]pyridine];

R-(−)-5'-(2-furanylmethyl)aminospiro[1-azabicyclo [2.2.2]octane-3,2'-(3'H)-furo[2,3-b]pyridine];

R-(−)-5'-(3-furanylmethyl)aminospiro[1-azabicyclo [2.2.2]octane-3,2'-(3'H)-furo[2,3-b]pyridine];

R-(−)-5'-(2-thienylmethyl)aminospiro[1-azabicyclo [2.2.2]octane-3,2'-(3'H)-furo[2,3-b]pyridine];

R-(−)-5'-(2-imidazolylmethyl)aminospiro[1-azabicyclo [2.2.2]octane-3,2'-(3'H)-furo[2,3-b]pyridine];

R-(−)-5'-N-(3-pyridyl)aminospiro[1-azabicyclo[2.2.2]octane-3,2'(3'H)-furo[2,3-b]pyridine];

R-(−)-5'-N-(3-thienylmethyl)aminospiro[1-azabicyclo [2.2.2]octane-3,2'-(3'H)-furo[2,3-b]pyridine];

R-(−)-5'-N-(2-imidazol-4-ylmethyl)aminospiro[1-azabicyclo[2.2.2]octane-3,2'-(3'H)-furo[2,3-b]pyridine];

R-(−)-5'-N-(thiazol-2-ylmethyl)aminospiro[1-azabicyclo [2.2.2]octane-3,2'-(3'H)-furo[2,3-b]pyridine];

R-(−)-5'-N-[trans-3-(4-pyridinyl)prop-2-enyl]aminospiro [1-azabicyclo[2.2.2]octane-3,2'-(3'H)-furo[2,3-b]pyridine]:

R-(−)-5'-N-acetyl-N-(3-thienylmethyl)aminospiro[1-azabicyclo[2.2.2]octane-3,2'-(3'H)-furo[2,3-b]pyridine];

R-(−)-5'-N-methyl-N-(4-pyridylmethyl)aminospiro[1-azabicyclo[2.2.2]octane-3,2'-(3'H)-furo[2,3-b]pyridine], or R-(−)-5'-N-methyl-N-(3-pyridylmethyl)aminospiro[1-azabicyclo[2.2.2]octane-3,2'-(3'H)-furo[2,3-b]pyridine];

or an enantiomer thereof, or a pharmaceutically-acceptable salt thereof.

4. A compound of formula I,

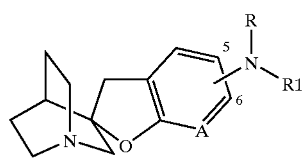

wherein $NRR^1$ is attached at the 5- or 6-position of the furopyridine ring;

R is hydrogen, $C_1$–$C_4$alkyl, or $COR^2$;

$R^1$ is $(CH_2)_nAr$, $CH_2CH$═CHAr, or $CH_2C$≡CAr;

n is 0 to 3;

A is N;

Ar is a 8-, 9- or 10-membered fused aromatic or heteroaromatic ring system containing zero to four nitrogen atoms, zero to one oxygen atoms, and zero to one sulfur atoms which fused aromatic or heteroaromatic ring system is optionally substituted with one to two substituents independently selected from: halogen, trifluoromethyl, or $C_1$–$C_4$alkyl;

$R^2$ is hydrogen, $C_1$–$C_4$alkyl; $C_1$–$C_4$alkoxy; or a phenyl ring optionally substituted with one to three of the following substituents: halogen, $C_1$–$C_4$alkyl, $C_2$–$C_4$alkyenyl, $C_2$–$C_4$alkynyl, OH, —$OC_1$–$C_4$alkyl, —$CO_2R^5$, —CN, —$NO_2$, —$NR^3R^4$, or —$CF_3$;

$R^3$, $R^4$ and $R^5$ are independently hydrogen; $C_1$–$C_4$alkyl; or a phenyl ring optionally substituted with one to three of the following substituent: halogen, $C_1$–$C_4$alkyl, $C_2$–$C_4$alkenyl, $C_2$–$C_4$alkynyl, —OH, or —$OC_1$–$C_4$alkyl, —CN, —$NO_2$, or —$CF_3$;

or an enantiomer thereof, or a pharmaceutically acceptable salt thereof.

5. A compound according to claim 4, wherein $R^1$ is —$CH_2CH$═CHAr.

6. A compound according to claim 4, wherein $R^1$ is —$CH_2C$≡CAr.

7. A compound according to claim 4, wherein $R^1$ is —$(CH_2)_n$Ar.

8. A compound according to claim 4, said compound being:

R-(−)-5'-N-(quinolin-3-ylmethyl)aminospiro[1-azabicyclo[2.2.2]octane-3,2'-(3'H)-furo[2,3-b]pyridine];

R-(−)-5'-N-(quinolin-4-ylmethyl)aminospiro[1-azabicyclo[2.2.2]octane-3,2'-(3'H)-furo[2,3-b]pyridine], or R-(−)-5'-N-(1,4-benzodioxan-6-ylmethyl)aminospiro[1-azabicyclo[2.2.2]octane-3,2'-(3'H)-furo[2,3-b]pyridine];

or an enantiomer thereof, or a pharmaceutically acceptable salt thereof.

9. A compound according to claim 4, wherein Ar is selected from 1-, or 2-naphthyl, 2-, 3-, 4-, 5-, 6-, 7-, or 8-quinolyl, 1-, 3-, 4-, 5-, 6-, 7-, or 8-isoquinolyl, 2-, 4-, 5-, 6-, or 7-benzoxazolyl, or 3-, 4-, 5-, 6-, or 7-benzisoxazolyl, or an enantiomer thereof, or a pharmaceutically acceptable salt thereof.

10. A pharmaceutical composition comprising a compound according to claim 4, in admixture with an inert pharmaceutically-acceptable diluent or carrier.

* * * * *